(12) United States Patent
Schroeder et al.

(10) Patent No.: US 6,193,749 B1
(45) Date of Patent: *Feb. 27, 2001

(54) CALCIFICATION-RESISTANT BIOMATERIALS

(75) Inventors: Richard F. Schroeder, Oakdale; Matthew F. Ogle, St. Paul, both of MN (US)

(73) Assignee: St. Jude Medical, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/931,930

(22) Filed: Sep. 17, 1997

Related U.S. Application Data

(63) Continuation of application No. 08/595,402, filed on Feb. 5, 1996, now abandoned.

(51) Int. Cl.$^7$ ............................................. A61F 2/02
(52) U.S. Cl. .................. 623/1.42; 623/1.48; 623/2.42; 623/926
(58) Field of Search .............................. 623/1, 2, 11, 901, 623/1.42, 1.46, 1.48, 2.42, 926; 8/94.11

(56) References Cited

U.S. PATENT DOCUMENTS

| | | | |
|---|---|---|---|
| 4,167,045 | * 9/1979 | Sawyer | 623/2 |
| 4,378,224 | * 3/1983 | Nimni et al. | 8/94.11 |
| 4,753,652 | * 6/1988 | Langer et al. | |
| 4,770,665 | * 9/1988 | Nashef | 623/2 |
| 5,094,661 | 3/1992 | Levy et al. | |
| 5,104,405 | * 4/1992 | Nimni | 623/2 |
| 5,215,541 | * 6/1993 | Nashef et al. | 623/2 |
| 5,368,608 | 11/1994 | Levy et al. | |
| 5,443,813 | 8/1995 | Hainfeld | |
| 5,509,932 | * 4/1996 | Keogh et al. | 623/2 |
| 5,693,085 | * 12/1997 | Buirge et al. | 623/1 |
| 5,697,967 | * 12/1997 | Dinh et al. | 623/11 |
| 5,797,887 | * 8/1998 | Rosen et al. | 604/65 |
| 5,984,905 | * 11/1999 | Dearnaley | 623/11 |
| 6,013,106 | * 1/2000 | Tweden et al. | 623/11 |

FOREIGN PATENT DOCUMENTS

| | | |
|---|---|---|
| 0 121 008 A2 | 10/1984 | (EP). |
| WO 88/01155 | 2/1988 | (WO). |
| WO 94/01481 | 1/1994 | (WO). |
| WO 95/11047 | 4/1995 | (WO). |

OTHER PUBLICATIONS

Bamberger et al., "Inhibition of Alkaline Phosphatase by Beryllium and Aluminum", Archives of Biochemistry and Biophysics, vol. 123, pp. 195–200 (1968).

Joshi et al., "Ferritin: An Iron Storage Protein With Diverse Functions", BioFactors, vol. 1, No. 3, pp. 207–212 (1988).

Levy et al., "Initiation of Mineralization in Bioprosthetic Heart Valves: Studies of Alkaline Phosphatase Activity and its Inhibition by $AlCl_3$ $FeCl_3$ Preincubations", J. Bio Mater. Res., V. 25, pp. 905–935 (1991).

Spiro et al., "The Hydrolytic Polymerization of Ferric Citrate. I. The Chemistry of the Polymer", Journal of the American Chemical Society, vol. 89, No. 22, pp. 5555–5559 (1967).

Johnston et al., "Prevention of Calcification of Bioprosthetic Heart Valve Leaflets by $Ca^{2+}$ Diphosphonate Pretreatment", Journal of Pharmaceutical Sciences, vol. 77, No. 9, pp. 740–744 (Sep. 1988).

Vyavahare et al., "Synergism of Calcium–Ethanehydroxybisphosphonate (CaEHbp) and $FeCl_3$: Controlled Release Polymers for Preventing Calcification of Bioprosthetic Aortic Wall", Journal of Controlled Release, vol. 34, No. 2, pp. 97–108 (May 1995).

Webb et al., "Aminodiphosphonate or $Al^{+++}$ Preincubation Inhibits Calcification of Aortic Homografts in the Rat Subdermal Model", ASAIO Transaction, vol. 34, No. 3, pp. 851–854 (Jul./Sep. 1988).

Webb et al., "Long–Term Efficacy of $Al^{3+}$ for Prevention of Bioprosthetic Heart Valve Calcification", ASAIO Transactions, vol. 36, No. 3, pp. 408–410 (Jul./Sep. 1990).

\* cited by examiner

*Primary Examiner*—Paul B. Prebilic
(74) *Attorney, Agent, or Firm*—Peter S. Dardi; Westman, Champlin & Kelly, P.A.; Hallie A. Funucane

(57) ABSTRACT

In general, the invention features a bioprosthetic article including a biocompatible material having at least one bound exogenous storage structure, the storage structure having a quantity of calcification inhibitors releasably bound thereto. The storage structure can be a protein or a synthetic polymer. The calcification inhibitors include metal ions and phosphatase inhibitors generally. Bifunctional metal chelators can be bound to endogenous proteins to deliver metal ions.

20 Claims, No Drawings

CALCIFICATION-RESISTANT BIOMATERIALS

This is a continuation of application Ser. No. 08/595,402, filed Feb. 5, 1996, now abandoned.

BACKGROUND OF THE INVENTION

The invention relates to prosthetic material that is treated to reduce calcification. More particularly, the invention relates to prosthetic material which is complexed with slowly released calcification inhibitors.

Bioprostheses, i.e., bioprosthetic devices, are used to repair or replace damaged or diseased organs, tissues and other structures in humans and animals. Bioprostheses must be generally biocompatible since they are typically implanted for extended periods of time. Specifically, bioprostheses can include artificial hearts, artificial heart valves, ligament repair material, vessel repair, surgical patches constructed of mammalian tissue and the like. Bioprostheses can be constructed from a combination of natural or synthetic materials.

Calcification, i.e., the deposit of calcium salts especially calcium phosphate (hydroxyapatite), occurs in and on some materials used in the production of implantable bioprostheses. This affects the performance and structural integrity of medical devices constructed from these biomaterials, especially over extended periods of time. For example, calcification is the primary cause of clinical failure of bioprosthetic heart valves made from porcine aortic valves or bovine pericardium. Calcification also significantly affects the performance of bioprostheses constructed from synthetic materials, such as polyurethane.

The importance of bioprosthetic animal heart valves as replacements for damaged human heart valves has resulted in a considerable amount of attention directed to the effects of calcification on these xenotransplants. Bioprosthetic heart valves from natural materials were introduced in the early 1960's and are typically derived from pig aortic valves or are manufactured from other biological materials such as bovine pericardium. Xenograft heart valves are typically fixed with glutaraldehyde prior to implantation to reduce the possibility of immunological rejection. Glutaraldehyde reacts to form covalent bonds with free amino groups in proteins, thereby chemically crosslinking nearby proteins.

Generally, bioprosthetic heart valves begin failing after about seven years following implantation, and few bioprosthetic valves remain functional after 20 years. Replacement of a degenerating valve prosthesis subjects the patient to additional surgical risk, especially in the elderly and in situations of emergency replacement. While failure of bioprostheses is a problem for patients of all ages, it is particularly pronounced in younger patients. Over fifty percent of bioprosthetic valve replacements in patients under the age of 15 fail in less than five years because of calcification.

Similarly, calcification of polyurethane bladders in artificial hearts and of leaflets in polyurethane valves is potentially clinically significant. Other bioprostheses made from natural and/or synthetic materials display clinically significant calcification.

As a result, there is considerable interest in preventing the deposit of calcium on implanted biomaterials, especially heart valves. Research on the prevention of calcification has focused to a considerable extent on the pretreatment of the biomaterial prior to implantation. Detergents (e.g., sodium dodecyl sulfate), toluidine blue or diphosphonates have been used to pretreat tissues in an attempt to decrease calcification by reducing calcium nucleation. These materials tend to wash out of the bioprosthetic material rather rapidly into the body fluids surrounding the implant, limiting their effectiveness.

Another approach to reducing calcification has been to remove at least some of the reactive glutaraldehyde moieties from the tissue by a chemical process. Still other approaches have included development of alternative fixation techniques, since evidence suggests that the fixation process itself contributes to calcification and the corresponding mechanical deterioration. In addition, since nonviable cells present in transplanted tissue are sites for calcium deposition, various processes have been developed to remove cellular material from the collagen—elastin matrix of the tissue prior to implantation.

A significant advance toward reducing calcification of bioprostheses was the determination that $Al^{+3}$ cations and other multivalent cations inhibit calcification. Bioprosthetic materials were treated with an acidic, aqueous solution of $AlCl_3$ prior to implantation. While some of the $Al^{+3}$ cations wash away after being removed from the treatment solution, a significant amount of cations remain associated with the treated materials for extended periods of time, presumably due to some type of association of the cations with the bioprosthetic material. It appears that the loading of ions into the material reaches a limiting value.

The associated $Al^{+3}$ cations are found to contribute to significant inhibition of the deposit of calcium. Furthermore, this effect persisted over a significant period of time, at least several months in a juvenile animal. Treatment with $Fe^{+3}$ salts is observed to produce similar effectiveness in reducing calcification.

It has been proposed that alkaline phosphatase is involved in the calcification of bioprostheses. Calcification seems related to cellular destruction and the corresponding disruption of cellular calcium regulation that maintains low intracellular calcium concentrations due to the pumping of $Ca^{+2}$ out of the cell. Cellular damage results from mechanical damage, extreme pH, extreme ionic concentration and/or chemical fixation, such as glutaraldehyde treatment. The cellular damage results in an uncontrolled influx of calcium into the nonviable cells.

Physiologically normal calcification of skeletal and dental tissues and pathological calcification, such as calcification of bioprostheses, have important similarities including the initial deposit of apatitic mineral. These mineral deposits contain calcium and phosphates, and mineral growth takes place at nuclei provided by initial deposits. Nucleation in bone development takes place at structures that have a high concentration of calcium binding phospholipids and high activity of phosphatases, especially alkaline phosphatase. Alkaline phosphatase activity is particularly high in children, which may contribute to the severe calcification problem for bioprostheses implanted into young patients.

Phosphatase activity is found to be inhibited by incubation with $AlCl_3$ and $FeCl_3$. This result suggests that the effect of $Al^{+3}$ and $Fe^{+3}$ cations in reducing calcification is due to the inhibition of the phosphatase activity. Alternatively or in addition, the ions may act by substitution into the hydroxyapatite crystal lattice which could prevent growth by destabilizing the crystal.

SUMMARY OF THE INVENTION

In general, the invention features a bioprosthetic article including a biocompatible material having at least one bound exogenous storage structure, the storage structure having a quantity of calcification inhibitors releasably bound thereto. The biocompatible material can include natural tissue. The natural tissue can be selected from the group consisting of porcine heart valves, aortic roots, walls, and or leaflets; and bovine pericardial tissues, connective tissue such as dura mater, homograft tissue, bypass grafts, tendons, ligaments, skin patches, blood vessels, human umbilical tissue, and bone. Alternatively or additionally, the biocompatible material can include a polymer.

The storage structure can be a protein, such as ferritin. The storage structure can be a synthetic polymer. The calcification inhibitor associated with the storage structure include a metal cation. The metal cations preferably are selected from the group consisting of $Al^{+3}$, $Fe^{+3}$, and $Mg^{+2}$. The calcification inhibitor also include diphosphates and phosphatase inhibitors. The phosphatase inhibitor preferably is selected from the group consisting of phosphate ions, $Ga^{+3}$, $La^{+3}$, borate ions, oxalate ions, cyanide ions, L-phenylalanine, urea, excess $Zn^{+2}$, glycine, propylamine, lavamisole and arsenate ions.

In the bioprosthetic article, the binding of the storage structure to the biocompatible material preferably is primarily covalent in character. Alternatively, the bioprosthetic article preferably has binding of the storage structure to the biocompatible material that is characterized by a plurality of non-covalent interactions. The exogenous storage structure preferably further includes a targeting molecule.

In a related aspect, the invention features a method of preparing biocompatible material, where the method includes binding a plurality of exogenous macromolecular storage structures to the biocompatible material, the macromolecular storage structures having a quantity of calcification inhibitor releasably bound thereto In a preferred method, the binding is performed by chemically crosslinking said macromolecular storage structures to said biocompatible material. In another preferred embodiment, the binding is performed by targeting using an adhesion molecule.

In another preferred method, the method further includes the step of contacting the biocompatible material with metal ions.

In another related aspect, a bioprosthetic article includes a biocompatible material having bound bifunctional chelators having a quantity of metal cations releasably bound thereto.

An advantage of the present invention is the capability of directing the calcification inhibitor to a selected portion of the biocompatible material. Another advantage of the present invention is the possibility of increasing the loading of calcification inhibitor in the material. Still another advantage of the present invention is the capability to select for a desired release time for the calcification inhibitor. Another advantage is the capability of processing the biocompatible material under approximate physiological conditions.

The invention provides for the use of a wide range of anti-calcification agents while providing for timed release into the microenvironment of the biocompatible material. Still another advantage of the invention is the combined use of exogenous storage structures with the placement of the biocompatible material in direct contact with a calcification inhibitor.

Other advantages and features of the invention will be apparent from the detailed description and from the claims.

DETAILED DESCRIPTION

Bioprostheses of the invention are constructed from biocompatible material that have bound structures that store calcification inhibiting agents. The slow release of these agents from the storage structures over time inhibits the deposit of calcium salts, especially calcium phosphate, on the biocompatible material. The use of bound storage structures containing the calcification inhibiting agents provides considerable versatility through selection of particular storage structures and bound calcification inhibiting agents.

Any degree of inhibition of calcium deposition is useful, given the clear association between calcification and deterioration of bioprostheses. A preferred degree of inhibition reduces the calcium deposition by at least about 50 to 75 percent over a two month period, compared to an untreated bioprosthesis. A more preferred degree of inhibition reduces the calcium deposition by at least 90 percent for a period greater than two months.

The methods of preparing the biocompatible materials with the storage structures can use conditions approximating physiological conditions. Depending on the selection of the storage structure and the attachment of the storage structures to the biocompatible material, amounts of calcification inhibitor in the bioprosthesis matrix can be relatively very large. The calcification inhibiting agents generally can be selected to inhibit calcium formation and specifically can be selected to inhibit the action of enzymatic precursors to hydroxyapatite formation, such as alkaline phosphatase. A plurality of different storage structures holding one or more calcification inhibitors can be used in a single bioprosthesis.

A. Biocompatible Materials

A bioprosthesis (bioprosthetic article) of the present application is a device that is implanted within the body of a host human or animal. The bioprosthesis is made from one or more biocompatible materials, and may be suitable for long term implantation within the host. It may be useful to provide the host with immuno suppressant treatments, although this treatment often will not be necessary. At least one of these biocompatible materials may have bound storage structures. The storage structures store a quantity of a calcification inhibiting agent or agents.

The biocompatible material preferably includes biological material or polymeric material. Some prostheses may be composed completely of metal components, and these prostheses generally will not be relevant for this invention. Bioprostheses within the invention may be comprised of a mixture of materials, such as metal portions along with portions of biological material and/or synthetic polymers. Relevant bioprostheses include without limitation artificial hearts, artificial heart valves, ligament repair material, bypass grafts, surgical patches constructed of mammalian tissue, and the like.

Biological material for use in the invention includes relatively intact tissue as well as decellularized tissue. These tissues may be obtained from, for example, heart valves, aortic roots, walls, and or leaflets; and pericardial tissues such as pericardial patches, connective tissue such as dura mater, homograft tissue, bypass grafts, tendons, ligaments, skin patches, blood vessels, human umbilical tissue, bone and the like. Generally, the tissues include collagen-containing material derived from different animal species, typically mammalian. The biological tissue is typically but not necessarily soft tissue. Tissue samples are typically fixed to cross-link the tissue and provide mechanical stabilization by preventing enzymatic degradation of the tissue. Glutaraldehyde is typically used to fix the cells, but other fixatives can be used, such as epoxides and other difunctional aldyhydes.

Decellularized tissue can be produced that is composed primarily of a structural matrix with cellular material removed, such as the collagen and elastin structural matrix. The decellularization process can involve applications of enzymes, other chemicals and physical treatments. See, for example, copending U.S. patent application Ser. No. 08/424,218, incorporated in its entirety by reference herein.

Synthetic, biocompatible polymeric materials for use in bioprostheses of the present invention include synthetic polymers as well as purified and woven biological polymers. Synthetic polymers include polyamides (nylon), polyesters, polystyrene, polyacrylates, vinyl polymers (e.g., polyethylene, polytetrafluoroethylene, polypropylene and poly vinyl chloride), polycarbonate, polyurethane, poly dimethyl siloxane, cellulose acetate, poly methyl methacrylate, ethylene vinyl acetate, poly sulfone, nitrocellulose and similar copolymers. These synthetic polymeric materials can be woven into a mesh to form a matrix or substrate. Alternatively, the synthetic polymer materials can be molded or cast into selected forms. Purified biological polymers that can be appropriately formed into a substrate include polysaccharides (e.g., cellulose and starch), polyamino acids, collagen, gelatin and cat gut sutures.

B. Calcification Inhibitors

Biological materials and polymeric materials are susceptible to calcification to varying degrees depending on the composition and structure of the material. The mechanism of calcification is not completely understood, but it displays similarities to calcium deposition related to bone formation. It has been postulated that phosphatases, especially alkaline phosphatase, play a significant role in the pathological calcification process. See, R. J. Levy et al., 25 J. Biomedical Materials Research 905–935 (1991)

The invention involves the delivery of anti-calcification agents in a controlled manner at the cellular level within and around the particular bioprosthesis. Small total quantities of active agent can be delivered while being effective to reduce or inhibit calcification. While the quantities may be small, and therefore, for example, non-toxic relative to the recipient, they can represent relatively high loading relative to the local environment of the bioprosthesis containing the active compositions.

Calcification inhibiting agents include compounds that inhibit nucleation of calcification, as well as alkaline phosphatase inhibitors. See, U.S. Pat. No. 5,368,608 to Levy et al. The anti-calcification agent is preferably released over an extended period of time in order to significantly extend the useful life of the bioprosthesis. The release of the agent or agents above background concentrations would preferably extend over several months, and would more preferably extend over several years.

$Al^{+3}$, $Mg^{+2}$ and $Fe^{+3}$ ions have been demonstrated to be calcification inhibitors and, when delivered in a timed release fashion, are effective in reducing calcification of bioprostheses. Multivalent cations, such as $Ga^{+3}$, $La^{+3}$ etc., are also known to inhibit the function of enzymatic precursors to hydroxyapatite formation, such as alkaline phosphatase. The invention involves the controlled association and slow release of calcification inhibitors, including multivalent cations, within the biocompatible material.

$Be^{+2}$ ions are also known to inhibit phosphatase, although beryllium is relatively toxic. Other phosphatase inhibitors include phosphate ions, $Ga^{+3}$, $La^{+3}$, borate ions, oxalate ions, cyanide ions, L-phenylalanine, urea, excess $Zn^{+2}$, glycine, propylamine, lavamisole and arsenate ions. The functioning of alkaline phosphatase is also affected by the Mg/Zn ion ratios. Other calcification inhibitors include diphosphates.

C. Exogenous Storage Structures

Storage structures are used for the storage and slow release of calcification inhibiting agents. The storage structures preferably will be microscopic, macromolecular compositions generally known as microspheres, such as natural or synthetic proteins or appropriate synthetic polymers. It is to be understood, however, that aggregations of the preferred compositions need not be microscopic. The agents stored by the exogenous storage structures generally can be any calcification inhibiting agent, such as multivalent metal cations. The term "protein" is intended to mean not only amino acids linked by peptide linkages, but also conjugated proteins containing amino acids with carbohydrates, nucleic acids and/or lipids.

Biological materials treated with significant concentrations of $Al^{+3}$ cations in solution have associated $Al^{+3}$ cations. It is possible that the observed association of the $Al^{+3}$ cations with the natural biological substrates may be due to binding with naturally occurring ferritin. Ferritin is an iron storage protein that can store relatively large quantities of iron ions, several thousands of iron ions per protein molecule. Ferritin can also store similar but smaller quantities of $Al^{+3}$ and other non-ferrous ions. Naturally occurring ferritin may be crosslinked or otherwise bound to a protein or other biological or synthetic substrate during fixation.

The natural ferritin would very slowly release cations, such as $Al^{+3}$, $Fe^{+3}$, $Mg^{+2}$ or the like, into the local environment. The storage structures of the present invention are in addition or as an alternative to any naturally occurring structures, such as ferritin already present in the biocompatible material (endogenous ferritin). In this way, the effectiveness of the treatment can be enhanced through the use of storage structures supplied from external sources (exogenous storage structures such as exogenous ferritin).

Appropriate protein storage structures within the scope of the present invention include metal binding proteins such as ferritin, transferrin, hemoglobin, myoglobin, ceruloplasmin and hemocyanin as well as modified proteins with addition of bifunctional chelators to generate metal binding capability. Ferritin is the preferred metal binding protein because of its large storage capacity. Apoferritin (ferritin protein without bound metal) is a 24 subunit protein with a molecular weight of approximately 450,000, although the molecular weight varies depending on the species from which the ferritin was isolated. Isoferritins, related proteins with differing numbers of subunits, are also within the scope of the present invention.

The ferritin core can store between about 2000 and about 4500 iron ions. For example, horse spleen ferritin can bind about 4500 iron ions compared with about 2500 iron ions in human ferritin. The iron is stored within the core as ferric oxide or ferric hydroxyphosphate. Ferritin can also bind large quantities of other metal ions including ions of the following metals: Al, Mg, Be, Cu, Zn, V, Tb, Cd. Binding of these non-iron ions is enhanced by the simultaneous binding of a moderate quantity of iron ions. The binding of iron or non-iron metal ions occurs both in vitro and in vivo.

The selection of a particular storage structure can be based on its storage capacity and the release rate of the stored calcification inhibitor. For example, ferritin or other metal binding proteins generally need not be saturated in the metal ion of interest to be useful in the invention. The ferritin can be charged with, for example, $Al^{+3}$ by incubating purified ferritin with a relatively concentrated $AlCl_3$ solution. The binding to the protein can be accelerated by heating and by pH adjustment. After a sufficiently long incubation, the free metal can be removed by passing the solution over an ion exchange resin.

Instead of using a naturally occurring metal storage protein, other proteins can be modified to create metal binding capability. Preferred proteins have high molecular weight, such as immunoglobulins. Metal sequestering compounds can be covalently bonded to the protein.

Significant metal binding capability can be created by binding a bifunctional chelator, such as a polyaminocarboxylate or a polyaminophosphonate, to the protein as the metal sequestering compound. Preferred bifunctional chelators include electrophylic and nucleophilic moieties such as bromoacetamide, maleimide, inidoester, thiophthalimide, N-hydroxysuccinimyl ester, pyridyl disulfide, phenyl azide, o-acylisourea, diazonium hydrazine, carbonyl hydrazine, amino hydrazine, acyl hydrazine, diazonium semicarbazide, carbonyl semicarbazide, amino semicarbazide, acyl semicarbazide, thio semicarbazides and cyclic polyaminocarboxylates and cyclic polyaminophosphonates having 12 to 16 atom rings. The specific chelator can be selected to produce a desired release rate of the bound metal ions.

The bifunctional chelators generally can be covalently bonded to the protein by conventional methods. Typically, the covalent bonds will be formed between selected amino acid residues of the protein and a specific functional group in the chelator. The number of chelating agents bound to a protein will depend on the structures and the reaction conditions.

It is preferable to have at least one bifunctional chelator bound to each protein, and it is more preferable to have multiple bifunctional chelators bound to each protein. Metal ions can be bound to the chelator either before, at the time of, or after the covalent binding of the chelator to the protein. The reaction conditions may influence the selected order of the process.

An alternative to use of a metal storage protein is use of a synthetic organometallic polymer to store metal cations. For example, alkaline solutions of ferric citrate can form a polymer having a core of ferric hydroxide with citrate surrounding the core. See, T. G. Spiro et al., 89 J. Amer. Chem. Soc. 5555–5559 (1967). Another example of an organometallic polymer is vinylferrocene, which contains a plurality of $Fe^{+2}$ ions between aromatic rings along a carbon chain. Selenium containing polyesters, polyamides, polyureas and polyurethanes are well known and are also suitable for the present invention. Generally, a large number of these organometallic polymers have been characterized, and can be selected based on the desired metal ion and release rate.

The appropriate exogenous storage structures are not limited to structures appropriate for the storage of metal ions. Anti-calcification agents, specifically phosphatase inhibitors, include non-metallic compounds. Preferred macromolecular storage structures for the storage of organic agents are synthetic polymers.

The desired calcification inhibiting compound can either be a monomer within the polymer chain or can be bonded to a side group of the polymer. Whether the desired compound is covalently or noncovalently bound to the polymer, the polymer can be designed to degrade to yield the desired compound at a selected rate. The degradation can take place through a thermal process or through the interaction with the in vivo chemical and biochemical environment.

D. Binding of the Exogenous Storage Structures

Binding of the exogenous storage structures to the biocompatible material can involve specific binding interactions to target specific structures within the material. Alternatively, the binding can involve non-specific binding due, for example, to reaction with general crosslinking agents. The use of general crosslinking agents generally precludes exogenous storage structures from being concentrated at particular locations within the bioprosthetic material.

A typical example of a procedure for non-specific binding makes use of glutaraldehyde, which crosslinks proteins by way of its two aldehyde groups. The non-specific crosslinking to bind the exogenous storage structures to the bioprosthetic material can be performed simultaneously with the fixation of the tissue. Alternatively, the non-specific crosslinking to bind the exogenous storage structures can be performed as a separate step before or after the completion of the fixation process.

The targeting of particular locations can be useful since it has been observed that calcification tends to initiate in specific locations. Examples of suitable targets include nuclear membranes, cytoplasmic locations, plasma membranes and extracellular sites.

The character of the targeted binding can be covalent or can involve a plurality of non-covalent interactions such as hydrogen bonding, van der Waals interactions and molecular rearrangements, which characterize, for example, antibody-antigen, specific binding protein-receptor and enzyme-substrate associations. A preferred method of targeting a particular location involves covalent binding of a linker to the storage structure and association of the linker with the bioprosthetic material by a plurality of non-covalent interactions.

A variety of commercially available antibodies and other specific binding reagents may be used as linkers, i.e., targeting molecules, to target cellular or extracellular sites having certain specific receptors. Alternatively, cellular or extracellular components at a preferred location of a biological material can be isolated by conventional techniques. For example, nuclear membranes or a specific portion of the nuclear membrane corresponding to an antigen or groupings of antigens can be isolated. The isolated materials then are used to produce polyclonal or monoclonal antibodies by conventional techniques. The resulting antibodies are covalently bonded to the exogenous storage structure to prepare it for binding to the bioprosthetic material.

A storage structure having an attached antibody, or comparable targeting molecule is considered a "storage structure" for the purposes of the present application. The binding of compounds to antibodies is well established in the art, especially where the compound is a protein. Due to its high iron content, ferritin is commonly linked to antibodies to serve as an electron microscopy probe in the histology field. In a preferred embodiment, glutaraldehyde is used to crosslink the respective proteins, i.e., ferritin and immunoglobulin.

The present inventors have demonstrated that calcification initiates frequently in the vicinity of the nuclear membrane. Therefore, a preferred approach involves use of antibodies directed to the nuclear membrane or a portion of the nuclear membrane. In this way, the storage structures can be targeted to cellular structures particularly susceptible to early events of calcium deposition.

E. Combined Treatment

The binding of exogenous storage structures of the invention can be combined with the process of direct treatment with metal salt solutions. Metal salt concentrations of the salt solutions generally are between 0.00001 and 0.1 molar, and preferably between 0.001 and 0.1 molar. The contacting of the biocompatible material with the metal salt solutions can take place before, after or during the binding of the storage structures to the biocompatible material. Appropriate salts include without limitation aluminum chloride, aluminum chlorate, aluminum lactate, aluminum potassium sulfate, aluminum nitrate, ferric chloride, ferric nitrate, ferric bromide, ferric sodium edentate, ferric sulfate, and ferric formate.

The metal salts also can be incorporated into a polymer matrix used in the bioprosthesis. The metal salts are preferably added during the polymerization step such that they are incorporated into the polymer matrix. In this way, the calcification inhibitor is released at a controlled rate over an extended period of time. The exogenous storage structures are then bonded to the polymer matrix.

Calcium ion chelators preferably at concentrations between approximately 0.00001 M and approximately 0.1 M can be added to the metal salt solutions prior to treatment. For example, citrate salts and citric acid have been found to enhance synergistically the calcification inhibition effect of $Al^{+3}$ and $Fe^{+3}$ ions. Similarly, other calcium ion chelators such as diphosphonate salts, including without limitation ethanehydroxydiphosphonate (EHDP or etidronate) and aminopropanehydroxydiphosphonate, also produce a synergistic improvement in the anti-calcification effect of the $Al^{+3}$ and $Fe^{+3}$ ions. Higher or lower concentrations can be used in particular applications.

The selection of the exogenous storage structure may be effected by the combined treatment with metal salt solutions. For example, the release rate of a calcification inhibiting agent may be selected in the combined treatment to yield more effective inhibition or inhibition over a longer period of time.

F. Using Endogenous Proteins For Delivery of Cations

In the same way that exogenous proteins can be modified to create metal binding capability, endogenous proteins can be similarly modified. For example, the biocompatible materials can be bound to bifunctional chelators to store metal ions. Preferred bifunctional chelators include electrophylic and nucleophilic moieties such as bromoacetamide, maleimide, inidoester, thiophthalimide, N-hydroxysuccinimyl ester, pyridyl disulfide, phynyl azide, o-acylisourea, diazonium hydrazine, carbonyl hydrazine, amino hydrazine, acyl hydrazine, diazonium semicarbazide, carbonyl semicarbazide, amino semicarbazide, acyl semicarbazide, thio semicarbazides and cyclic polyaminocarboxylates and cyclic polyaminophosphonates having 12 to 16 atom rings. The specific chelator can be selected to produce the desired release rate of the bound metal ions.

The bifunctional chelators can be covalently bound to the endogenous proteins in the same way they would be bound to the exogenous proteins as described above in section C. The quantities of bifunctional chelators bound to the biocompatible materials can be selected to achieve the desired loading of calcification inhibitors in the material.

What is claimed is:

1. A bioprosthetic article comprising a biocompatible material and an exogenous storage structure that is bound to the biocompatible material, said storage structure comprising a metal binding protein and said storage structure having a quantity of calcification inhibitors releasably bound thereto.

2. The bioprosthetic article of claim 1, wherein said biocompatible material comprises natural tissue.

3. The bioprosthetic article of claim 2, wherein said natural tissue is selected from the group consisting of porcine heart valves, aortic roots, aortic walls, aortic leaflets, bovine pericardial tissues, connective tissues, dura matter, homograft tissue, bypass grafts, tendons, ligaments, skin patches, blood vessels, human umbilical tissue and bone.

4. The bioprosthetic article of claim 1, wherein said biocompatible material comprises a polymer.

5. The bioprosthetic article of claim 1, wherein said protein comprises ferritin.

6. The bioprosthetic article of claim 1, wherein said calcification inhibitor comprises a metal cation.

7. The bioprosthetic article of claim 6, wherein said metal cations are selected from the group consisting of $Al^{+3}$, $Fe^{+3}$, and $Mg^{+2}$.

8. The bioprosthetic article of claim 1, wherein said calcification inhibitor comprises a diphosphate.

9. The bioprosthetic article of claim 1, wherein said calcification inhibitor comprises a phosphatase inhibitor.

10. The bioprosthetic article of claim 9, wherein said phosphatase inhibitor is selected from the group consisting of phosphate ions, $Ga^{+3}$, $La^{+3}$, borate ions, oxalate ions, cyanide ions, L-phenylalanine, urea, $Zn^{+2}$, glycine, propylamine, lavamisole, and arsenate ions.

11. The bioprosthetic article of claim 1, wherein said binding of said storage structure to said biocompatible material is primarily covalent in character.

12. The bioprosthetic article of claim 1, wherein said binding of said storage structure to said biocompatible material is characterized by a plurality of non-covalent interactions.

13. The bioprosthetic article of claim 1, wherein said exogenous storage structure further comprises a targeting molecule.

14. A bioprosthetic article comprising a biocompatible material and an exogenous, attached protein with bound bifunctional chelators and with a quantity of multivalent metal cations releasably bound to the bifunctional chelators.

15. A bioprosthetic article comprising a biocompatible material and an exogenous metal binding protein that is bound to the biocompatible material, said protein having a quantity of calcification inhibitors bound thereto, wherein said protein has been modified to create metal binding capability.

16. The bioprosthetic article of claim 15, wherein said protein is a synthetic protein.

17. A bioprosthetic article comprising a biocompatible material and an exogenous, macromolecular storage structure that is bound to the biocompatible material, said storage structure having a quantity of calcification inhibiting multivalent metal cations releasably bound thereto, wherein the storage structure comprises a synthetic organometallic polymer.

18. The bioprosthetic article of claim 14 wherein the multivalent metal cations comprise ions selected from the group consisting of $Al^{+3}$, $Fe^{+3}$, and $Mg^{+2}$.

19. The bioprosthetic article of claim 14 wherein the multivalent cations comprise $Al^{+3}$.

20. The bioprosthetic article of claim 14 wherein the bifunctional chelator is selected from the group consisting of polyaminocarboxylate, polyaminophosphonate, bromoacetamide, maleimide, inidoester, thiophthalimide, N-hydroxysuccinimyl ester, pyridyl disulfide, phynyl azide, 0-acylisourea, diazonium hydrazine, carbonyl hydrazine, amino hydrazine, acyl hydrazine, diazonium semicarbazide, carbonyl semicarbazide, amino carbazide, acyl semicarbazide, thio semicarbazide, and cyclic polyaminocarboxylates and cyclic polyaminophosphonates having 12 to 16 atom rings.

* * * * *